(12) United States Patent
Tiemann et al.

(10) Patent No.: US 11,975,237 B2
(45) Date of Patent: May 7, 2024

(54) RESPIRATORY THERAPY SYSTEM AND METHOD OF OPERATING A RESPIRATORY THERAPY SYSTEM

(71) Applicant: Loewenstein Medical Technology S.A., Luxembourg (LU)

(72) Inventors: Bjoern Tiemann, Ahrensburg (DE); Christof Goebel, Hamburg (DE); Anne Wonsyld, Hamburg (DE); Thomas Ress, Barmstedt (DE); Benjamin Adametz, Hamburg (DE); Jan Schattner, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1112 days.

(21) Appl. No.: 16/226,815

(22) Filed: Dec. 20, 2018

(65) Prior Publication Data

US 2019/0269966 A1 Sep. 5, 2019

(30) Foreign Application Priority Data

Dec. 22, 2017 (DE) .......................... 102017011940.6

(51) Int. Cl.
*A61M 16/00* (2006.01)
*A61M 16/08* (2006.01)
(Continued)

(52) U.S. Cl.
CPC ............. *A63B 23/18* (2013.01); *A61M 16/00* (2013.01); *A61M 16/0006* (2014.02);
(Continued)

(58) Field of Classification Search
CPC .......... A61M 16/0003; A61M 2205/33; A61M 16/0009; A61M 16/00; A61M 16/0006;
(Continued)

(56) References Cited

U.S. PATENT DOCUMENTS

| 6,209,540 B1 | 4/2001 | Sugiura | |
|---|---|---|---|
| 2005/0056283 A1* | 3/2005 | Levi | A61M 16/021 128/204.21 |

(Continued)

FOREIGN PATENT DOCUMENTS

| DE | 19914749 A1 | 12/1999 |
|---|---|---|
| WO | 2007054829 A2 | 5/2007 |

(Continued)

*Primary Examiner* — Justine R Yu
*Assistant Examiner* — Matthew R Moon
(74) *Attorney, Agent, or Firm* — Abel Schillinger, LLP (57) ABSTRACT

The present invention relates to a respiratory therapy system having two respiratory therapy devices operable separately and independently of one another. The respiratory therapy devices each have a control unit and each have a device component controllable by means of the control unit for providing a device function. In this case, a coupling unit is provided for establishing an operational connection between the respiratory therapy devices. The coupling unit is designed for the purpose of controlling the control units of the respiratory therapy devices when the operational connection is established.

15 Claims, 4 Drawing Sheets

(51) Int. Cl.
   *A61M 16/14* (2006.01)
   *A61M 16/20* (2006.01)
   *A63B 23/18* (2006.01)

(52) U.S. Cl.
   CPC .... *A61M 16/0009* (2014.02); *A61M 16/0066* (2013.01); *A61M 16/024* (2017.08); *A61M 16/0816* (2013.01); *A61M 16/14* (2013.01); *A61M 16/20* (2013.01); *A61M 16/204* (2014.02); *A61M 16/205* (2014.02); *A61M 2205/056* (2013.01); *A61M 2205/35* (2013.01); *A61M 2205/502* (2013.01); *A61M 2205/583* (2013.01); *A61M 2205/586* (2013.01)

(58) Field of Classification Search
   CPC ............ A61M 16/024; A61M 16/0066; A61M 16/0816; A61M 16/14; A61M 16/20; A61M 16/205; A61M 2205/586; A61M 2205/35; A61M 2205/502; A61M 16/204; A61M 2205/056; A61M 2205/583; A61M 2205/505; A61M 2209/084; A63B 23/18; A61G 12/008; G06F 3/1423
   See application file for complete search history.

(56) References Cited

U.S. PATENT DOCUMENTS

| | | |
|---|---|---|
| 2007/0186928 A1 | 8/2007 | Be'eri |
| 2007/0199566 A1* | 8/2007 | Be'eri ............... A61M 16/0069 128/204.23 |
| 2008/0149099 A1 | 6/2008 | Doyle |
| 2012/0199127 A1* | 8/2012 | Garde ................ A61M 16/024 128/204.23 |
| 2016/0067434 A1* | 3/2016 | Schwaibold ...... A61M 16/0051 128/202.22 |
| 2017/0215979 A1* | 8/2017 | Childs ................. A61M 5/1415 |

FOREIGN PATENT DOCUMENTS

| | | |
|---|---|---|
| WO | 2008008659 A2 | 1/2008 |
| WO | 2017144963 A2 | 8/2017 |

* cited by examiner

RESPIRATORY THERAPY SYSTEM AND METHOD OF OPERATING A RESPIRATORY THERAPY SYSTEM

CROSS-REFERENCE TO RELATED APPLICATIONS

The present application claims priority under 35 U.S.C. § 119 of German Patent Application No. 102017011940.6, filed on Dec. 22, 2017, the entire disclosure of which is expressly incorporated by reference herein.

BACKGROUND OF THE INVENTION

1. Field of the Invention

The present invention relates to a respiratory therapy system having at least two respiratory therapy devices operable separately and independently of one another and a method of operating such a respiratory therapy system.

2. Discussion of Background Information

For successful ventilation or coughing assistance, it is generally particularly important for the respiratory therapy devices used to be adapted to the individual needs of the patient. Moreover, the most accurate possible observation and/or monitoring of the progress of therapy is of great importance. For this purpose, the devices used often have operating elements and an integrated monitor, on which the profile of specific respiration parameters is displayed. However, the known devices have the disadvantage that the adaptations to the needs of the respective patient are frequently very complex and time-consuming. For patients who require both ventilation and also coughing assistance, the effort is still greater. Moreover, the display on the integrated monitors is often very restricted and confusing, since the resulting devices are to be as compact as possible.

Therefore, respiration devices have become known in the prior art which are connected to a network. Thus, settings can be performed and data can be displayed using a central computer. However, the operation and analysis directly at the devices still remains restricted and/or confusing.

A further problem is that a corresponding device which offers all functions necessary for optimum treatment of the patient is not always available. For this purpose, either a great number of different devices or very extensively equipped devices have to be available, which is accompanied by a high cost expenditure.

It would therefore be advantageous to improve the use of respiratory therapy devices. In this case, in particular an improved treatment is to be enabled and the effort for the operation of respiratory therapy devices is to be reduced at the same time.

SUMMARY OF THE INVENTION

The present invention provides a respiratory therapy system and a method of operating a respiratory therapy system as specified in the independent claims. Preferred refinements are the subject matter of the dependent claims. Further advantages and features of the present invention result from the general description and the description of the exemplary embodiments.

The respiratory therapy system according to the invention comprises at least two respiratory therapy devices operable separately and independently of one another. The respiratory therapy devices each have at least one control unit and at least one device component controllable by means of the control unit for providing at least one device function. In this case, at least one coupling unit is provided for establishing an operational connection between the at least two respiratory therapy devices. The coupling unit is suitable and designed for the purpose of controlling the control units of the at least two respiratory therapy devices when the operational connection is established. By means of the coupling unit, at least one device component of the at least one respiratory therapy device is at least partially functionally expandable and/or at least partially functionally replaceable by at least one device component of the at least one other respiratory therapy device.

The respiratory therapy system according to the invention offers many advantages. One significant advantage is that the device function of one respiratory therapy device can be supplemented and/or replaced by a device function of the other respiratory therapy device. The available devices thus do not always have to have all required functions, since they can supplement one another accordingly. Thus, for example, a device having fewer functions can be coupled to a device having a presently needed function, to achieve optimum care of the patient. Since two or more devices having the full functional scope do not have to be kept ready, substantial costs can be saved. At the same time, the care of the patient can be functionally expanded. One special advantage of the invention is moreover that the respiratory therapy devices can also be used alone and/or independently of one another. Moreover, the operation and analysis can be substantially simplified by the functional supplementation and/or expansion.

The respiratory therapy system particularly preferably comprises at least two different types of respiratory therapy devices. In particular, the at least two respiratory therapy devices are designed differently and preferably comprise different device components and/or different device functions. The at least two respiratory therapy devices can also be similar or identical.

The respiratory therapy system preferably comprises at least one respiratory therapy device designed as a ventilator and at least one respiratory therapy device designed as a coughing device. The respiratory therapy system offers particularly many advantages due to being equipped with such devices. Optimum care of the patient during ventilation and during coughing assistance or coughing maneuvers can thus be carried out, without both devices having to have a full functional scope. The respiratory therapy system can also comprise at least one other type of respiratory therapy device.

In particular, the one respiratory therapy device is provided by the ventilator and the other respiratory therapy device is provided by the coughing device. It is also possible and preferable for one respiratory therapy device to be provided by the coughing device and the other respiratory therapy device to be provided by the ventilator. The at least two respiratory therapy devices can also be designed as two coughing devices or as two ventilators, however.

The coughing device is used in particular for the targeted assistance of secretion removal from the airways of a patient. The coughing device comprises in particular at least one coughing unit for generating at least one respiratory airflow for an insufflation into the patient and/or at least one respiratory airflow for an exsufflation out of the patient. The ventilator comprises in particular at least one ventilating unit for generating at least one respiratory airflow for ventilating a patient. The coughing unit and/or the ventilating unit comprises in particular at least one blower unit and/or a device for pressure specification and/or a device for volume specification.

In a preferred embodiment, at least one display unit of the at least one respiratory therapy device is at least partially functionally expandable and/or replaceable by at least one display unit of the at least one other respiratory therapy device. For example, settings of parameters are carried out on one device while the display is output via a display of the other device. A data visualization can thus be expanded and/or replaced. A substantially improved representation of data and/or items of information directly at the respiratory therapy devices is thus possible. The caregiver thus does not first have to change to a computer having a correspondingly large monitor to obtain a comprehensive representation of the data.

The display unit is used in particular for data visualization. The display unit in particular comprises at least one display and/or at least one monitor and/or at least one display screen or the like.

The display unit can also provide at least one operating unit and is then preferably designed as a touchscreen or the like. In particular, the display unit is used for visualizing device parameters and/or respiration parameters. In particular, different data visualizations are displayable on the coupled display units. In particular, at least one monitor of the at least one respiratory therapy device is used as an additional monitor for the at least one respiratory therapy device. For example, the monitor of the coughing device is used as an additional monitor for the ventilator.

It is possible that the display units of the operationally connected and/or separate respiratory therapy devices can each be oriented or are oriented in consideration of a spatial location of the respiratory therapy device. The user can thus set up the device optimally for himself, without thus having to accept losses in the observation of the display unit. The orientation of the display units is performed automatically in particular. It is also possible that the orientation is performed after an input of an item of information about the spatial location.

Preferably, at least one operating unit of the at least one respiratory therapy device is at least partially functionally expandable and/or replaceable by at least one operating unit of the at least one other respiratory therapy device. This has the advantage that, for example, operation and/or control or also a data input of one respiratory therapy device can be supplemented and/or replaced by an operation and/or control or data input of the other respiratory therapy device. The operating unit comprises in particular at least one input device and/or one human interface device. The operating unit comprises, for example, at least one switch and/or at least one keyboard and/or mouse and/or at least one touchscreen and/or at least one touchpad or the like. The operating unit can be at least partially integrated into a display unit.

The replaced operating unit is deactivatable in particular. In particular, an automatic deactivation occurs upon establishment of the operational connection. It is also possible that the deactivation of the operating unit is performed after a user input. A simultaneous operation of both operating units can also be provided.

In particular, the operating unit of a ventilator is expandable and/or replaceable by an operating unit of a coughing device. It is also possible that an operating unit of a coughing device is expandable and/or replaceable by an operating unit of a ventilator.

In particular, a therapy unit of the at least one other respiratory therapy device is controllable from the operating unit of the at least one respiratory therapy device. In particular, the therapy unit comprises at least one ventilating unit and/or at least one coughing unit. The setting of the therapy unit thus becomes substantially more comfortable. In particular, the one respiratory therapy device also comprises at least one therapy unit, which in particular comprises at least one coughing unit and/or at least one ventilating unit.

In particular, the therapy unit of the respective respiratory therapy device is also controllable from its operating unit. However, it is also possible that the operability of the therapy unit of the respective respiratory therapy device is deactivated or is deactivatable from its operating unit.

In particular, the therapy unit of the other respiratory therapy device is activatable and/or deactivatable and/or settable from the operating unit of the one respiratory therapy device. For example, a start and/or a stop of the therapy and, for example, a ventilation function and/or coughing function can be carried out. For example, settings of device parameters and/or ventilation parameters can also be performed. It is also possible that an automatic function and/or a manual function is selectable. In particular, the point in time of a start and/or stop and/or a pause and/or other corresponding parameters are settable.

In particular, at least one therapy unit of the at least one respiratory therapy device is at least partially functionally expandable and/or replaceable by at least one therapy unit of the at least one other respiratory therapy device. In this case, one of the two therapy units in particular comprises at least one ventilating unit. The other of the two therapy units comprises in particular at least one coughing unit. It is also possible that both therapy units comprise a ventilating unit and/or a coughing unit. Respiratory therapy devices can thus functionally supplement one another, to offer an optimum scope of therapy to the patient.

The therapy unit of the at least one respiratory therapy device can preferably be synchronized by means of the coupling unit with the therapy unit of the at least one other respiratory therapy device at least in consideration of at least one device parameter and/or ventilation parameter. The effort for a patient-specific adaptation of the devices can thus be substantially simplified. Thus, for example, only one device has to be set to the patient, while the other respiratory therapy device is synchronized and adapted via the coupling unit. For example, it is particularly helpful to synchronize a coughing unit with the settings of a ventilating unit. It is also particularly advantageous that the synchronization can be carried out directly on one or both respiratory therapy devices. An access via a remotely located computer can thus be dispensed with. Alternatively, the synchronization can also be carried out via a remotely located computer, which stores and compares required data. In particular, a coughing unit can be synchronized with a ventilating unit or vice versa.

In particular, at least one device parameter and/or ventilation parameter is transmittable from the one to the other respiratory therapy device or vice versa. In particular, an access from the one therapy unit to the other therapy unit is possible in this case, to retrieve and/or set the device parameter and/or ventilation parameter. In particular, the synchronization is carried out with established operational connection. An at least partially automatic and/or at least partially manual synchronization is possible. For example, it can be selected which device parameter and/or ventilation parameter is to be synchronized. It is also possible that the synchronized device parameter and/or ventilation parameter can be at least partially modified and/or adapted.

The therapy unit of the at least one respiratory therapy device is preferably suitable and designed for the purpose of at least partially controlling and in particular deactivating and/or activating and/or setting by means of the coupling unit at least one nebulizer unit arranged in the at least one other respiratory therapy device. The nebulizer unit can thus be used for both devices, without having to actually be installed in both devices. The nebulizer unit is in particular also controllable from the respiratory therapy device. For example, the nebulizer unit is arranged in a ventilating unit of a ventilator. In this case, the nebulizer unit is preferably controllable and usable for therapy by a coughing unit of a coughing device. A component other than the nebulizer unit can also be provided for this purpose.

The therapy unit of the at least one respiratory therapy device is particularly preferably suitable and designed for the purpose of controlling and in particular pneumatically controlling by means of the coupling unit an exhalation system of the at least one other respiratory therapy device. The exhalation system is connected in particular to the other respiratory therapy device. In particular, an exhalation system of a coughing device is controllable from a ventilator or vice versa. The respiratory therapy can be substantially improved by such a functional coupling.

The therapy unit of the at least one respiratory therapy device is preferably connectable to at least one expiration part or expiration block of the other respiratory therapy device to establish a flow connection, in order to be used as a partial vacuum unit for the exhalation in the expiration when the operational connection is established. The use as a partial vacuum unit for the exhalation in the expiration can be carried out in a time-dependent and/or input-dependent manner. The expiration part is in particular part of the therapy unit of the other respiratory therapy device. In this case, the one respiratory therapy device is in particular a coughing device. The other respiratory therapy device is designed in particular as a ventilator. An inverted embodiment is also possible. In particular, a coughing unit is connectable to the expiration part of the ventilator.

In one particularly advantageous embodiment, the coupling unit is suitable and designed for the purpose of at least partially deactivating and/or activating the device component of the at least one respiratory therapy device and/or the device component of the at least one other respiratory therapy device when the respiratory therapy devices are operationally connected. The operation of one device component can thus be saved if an operational connection is present. Thus, for example, a battery runtime can be substantially lengthened. For example, a blower unit or display unit or operating unit can be partially deactivated if the operationally-connected other device provides a corresponding component.

In particular, the device component is deactivatable by the coupling unit which is at least partially replaced and/or expanded by the other device component. A standby and/or an idle mode and/or a complete shutdown can be provided for the deactivation, for example. It is possible that the deactivation and/or activation can be carried out automatically and/or manually and, for example, by means of a user input.

An activation preferably takes place as soon as the use of the deactivated device component is recognized and/or requested. For example, a wake-up function is provided, for example, from an operating unit. In particular, the device component is activated if a request and/or operation takes place from the respiratory therapy device having the deactivated device component.

In a particularly preferred embodiment, the coupling unit comprises at least one receptacle apparatus for physically receiving the at least two respiratory therapy devices. The receptacle apparatus preferably has at least one receptacle unit for each of the respiratory therapy devices. It is also possible and preferable for the receptacle apparatus to have at least one common receptacle unit for the respiratory therapy devices. It is thus possible to work particularly comfortably and ergonomically with the operationally-connected devices. It is possible that with receiving of the respiratory therapy devices in the receptacle apparatus, an automatic establishment of the operational connection takes place and/or at least one user input for establishing the operational connection is requested. For example, the respiratory therapy devices and the receptacle apparatus can be equipped with a function in the manner of a plug-and-play. It is possible that the receptacle apparatus is suitable and designed for the purpose of automatically recognizing the type of the received respiratory therapy device. The coupling can also comprise an operational connection without a physical coupling of the respiratory therapy devices.

The receptacle units and/or the common receptacle unit can be designed as a wall mount and/or bed mount and/or wheelchair mount and/or table mount and/or as a chassis or the like.

It is possible that the respiratory therapy devices received in the receptacle apparatus can be arranged one over another and/or adjacent to one another and/or back-to-back. Such arrangements offer a particularly good access and/or particularly practical usage of the devices. Other suitable arrangements, for example in succession or the like, can also be provided. In particular, one of the at least two display units is deactivatable or deactivated when the respiratory therapy devices are arranged back-to-back. In particular, an automatic deactivation takes place and/or at least one user input is requested when the coupling mode back-to-back is recognized.

In particular, the display units are oriented in different directions and in particular toward opposite sides when the respiratory therapy devices are arranged back-to-back. In particular, the display units are oriented essentially in a common direction when the respiratory therapy devices are arranged one over another and/or adjacent to one another and/or in succession.

The method according to the invention is used for operating a respiratory therapy system having at least two respiratory therapy devices operable separately and independently of one another. The respiratory therapy devices each have at least one control unit and each have at least one device component controlled by the control unit. At least one device function is provided by the device component. In this case, at least one operational connection is established between the at least two respiratory therapy devices by means of at least one coupling unit. When the operational connection is established, the control units of the at least two respiratory therapy devices are at least temporarily activated. At least one device component of the at least one respiratory therapy device is at least partially functionally expanded and/or at least partially functionally replaced by at least one device component of the at least one other respiratory therapy device.

The method according to the invention also offers many advantages. It is particularly advantageous that the coupled respiratory therapy devices are functionally expanded and/or supplemented. A substantially improved functionality and treatment quality is thus achieved in relation to separately used devices.

The method is used in particular for operating the above-described respiratory therapy system. In particular, the respiratory therapy system according to the invention is suitable and designed for the purpose of being operated as per the method according to the invention.

Data of the one respiratory therapy device are preferably visualized on at least one display unit of the other respiratory therapy device, so that at least one display unit of the one respiratory therapy device is supplemented and/or replaced. In particular, data of a ventilator are visualized on a display unit of a coughing device.

In particular, an established and/or active operational connection is indicated by means of at least one graphic and/or at least one symbol in the display unit of the one and/or the other respiratory therapy device. The user thus receives an indication that two display units are active or which display unit is available to him.

In this case, the data preferably relate to at least one device parameter and/or at least one ventilation parameter of a ventilation of a patient. The device parameter and/or the ventilation parameter are preferably graphically displayed. In particular, a graphic plot of the ventilation parameter and/or the device parameter is displayed as a function of time and/or as a function of another reference parameter. For example, a curve view is displayed. In particular, two or three or more device parameters and/or ventilation parameters are graphically displayed. A numeric representation and/or a representation in text form is also possible.

It is possible that data of one respiratory therapy device are simultaneously also visualized on its display units. It is also possible that the display unit of one respiratory therapy device is at least partially deactivated or is provided for displaying other items of information.

In particular, at least one display unit is used for the graphic display of a profile function of at least one device parameter and/or ventilation parameter. In particular, the other display unit is then used for the numeric and/or written representation of at least one device parameter and/or ventilation parameter.

In a particularly advantageous embodiment, at least one menu for controlling a ventilator is displayed on the one respiratory therapy device. In particular, a graphic representation of the ventilation parameter takes place simultaneously on the other respiratory therapy device. A graphic plot of the ventilation parameter as a function of time and/or as a function of another ventilation parameter particularly preferably takes place on the other respiratory therapy device. In this case, the other respiratory therapy device is preferably designed as a coughing device or vice versa. Such an embodiment has the advantage that the display units and/or a monitor of the coughing device can be used for visualizing data of the ventilator. The ventilator can thus be set via a particularly comprehensible menu and reliable monitoring of the ventilation parameter can take place simultaneously. If the coughing device is then used, for example, for a coughing maneuver, a changeover can be carried out automatically or manually, so that a menu for its control or the like is displayed on the display unit of the coughing device.

In one embodiment, a menu for controlling a coughing unit can be displayed on a respiratory therapy device designed as a coughing device. In this case, a graphic representation of a ventilation parameter and/or device parameter specific for the coughing maneuver can be carried out simultaneously on the other respiratory therapy device, which is designed in particular as a ventilator. Such a design offers an advantageous supplementation of the display unit of the coughing device with the display unit of the ventilator.

It is also possible that a menu for controlling a ventilator and/or a coughing unit is displayed on both display units. It is also possible that a graphic representation of the ventilation parameter and/or device parameter is carried out on both display units. It is possible that it is selected by means of a user input on which of the two respiratory therapy devices the menu for the control and/or the graphic representation of the ventilation parameter is to be produced.

In particular, an operation of the one respiratory therapy device is carried out on an operating unit of the other respiratory therapy device, so that an operating unit of the one respiratory therapy device is supplemented and/or replaced. In particular, an operation of a ventilator is performed on an operating unit of a coughing device. It is also possible that an operation of a coughing device is carried out on an operating unit of a ventilator. This offers an advantageous adaptation of the scope of the operating unit, so that settings and inputs can be performed very reliably and conveniently.

It is possible that the one respiratory therapy device comprises at least one remote control. In this case, the other respiratory therapy device is preferably operated by means of the remote control. For example, a ventilator is equipped with a remote control. If the ventilator is coupled to a coughing device, a coughing maneuver can preferably also be triggered by means of the remote control. An inverted embodiment is also possible.

At least one device function of the other respiratory therapy device is preferably started and/or stopped and/or set from the one respiratory therapy device. This can be carried out manually via an operating unit or automatically via a corresponding control command. For example, a coughing maneuver of a coughing device is started and/or stopped and/or set from a ventilator. It is also possible that a ventilation function of a ventilator is started and/or stopped and/or set from a coughing device.

In this case, a profile of pressure and/or flow and/or volume and/or oxygen saturation can be visualized in particular during the coughing maneuver by means of the display unit of the ventilator and/or the coughing device. It is also possible that a profile of pressure and/or flow and/or volume and/or oxygen saturation is visualized during a ventilation by means of the display unit of the coughing device and/or the ventilator.

It is possible and preferable that at least one device parameter and/or ventilation parameter for a device function is transmitted to the other respiratory therapy device from the one respiratory therapy device. In this case, the device function of the other respiratory therapy device is preferably adapted as a function of the transmitted device parameter or ventilation parameter, respectively, so that a synchronization or a parameter setting of the respiratory therapy devices is enabled. A coupled respiratory therapy device can thus be adapted very rapidly and also very reliably to the individual needs of a patient.

The parameter setting is particularly advantageous if a patient has to be supplied, for example, both with a coughing device and also with a ventilator. The setting of two devices would then be necessary in the prior art, which is accompanied by a corresponding time and work expenditure. It is possible by way of the invention presented here to set the second device rapidly and reliably by way of the parameter setting. If the patient is supplied with a ventilator, for example, and a coughing device is also to be added, complex setting is thus no longer necessary for the coughing device.

Additionally or alternatively, the transmission of the device parameter and/or the ventilation parameter can take place in the other direction. A two-sided transmission and/or a mutual synchronization is also possible. The device function relates in particular to a therapy function and, for example, a coughing maneuver and/or a ventilation. Other device functions are also possible, for example, display settings, operating settings, and/or configuration settings. A coughing maneuver or a coughing therapy is preferably adapted and/or synchronized in dependence on a ventilation. It is also possible that a ventilation is adapted and/or synchronized in dependence on the coughing therapy. In particular, the ventilator performs at least one parameter setting on a coughing device. It is also possible that the coughing device performs at least one parameter setting on a ventilator. In all embodiments, it is preferable for a coughing unit of a respiratory therapy device designed as a coughing device to be controlled and/or operated by a respiratory therapy device designed as a ventilator.

In particular, at least one respiration assistance is provided by the coughing unit during the ventilation. The respiration assistance is designed in particular as a coughing maneuver or comprises at least one such maneuver. The ventilation of a patient can thus be substantially improved. It is also possible that a respiration assistance is provided by means of a ventilating unit of the ventilation device during a coughing maneuver and/or between at least two coughing maneuvers.

In one advantageous embodiment, at least one point in time of an insufflation and/or an exsufflation and/or a pause is set from the ventilator. The coughing unit is preferably switched into at least one automatic mode from the ventilator, in which a coughing maneuver is triggered at least partially automatically. The coughing unit can also be operated at least partially manually from the ventilator, so that point in time and/or duration and/or other parameters of the coughing maneuver are settable by at least one user input.

During the control and/or operation of the coughing device from the ventilator, an operation on the coughing device itself can be deactivated or blocked. A parallel operation of the coughing device from both devices can also be provided.

In an advantageous embodiment, the ventilator carries out at least one coughing maneuver at least partially automatically by means of the coughing unit during a ventilation. It is also possible that the ventilator outputs at least one notification to a user in particular during a ventilation, which notifies of a coughing maneuver which is to be carried out and/or imminent. After the notification, a coughing maneuver can take place automatically. It is also possible to wait for a user input after the notification.

At least one nebulizer unit arranged in the ventilator can be activated before the coughing maneuver with respect to time, to prepare for the coughing up by nebulizing of medications in particular. Substantially more pleasant and effective coughing up can thus take place. Moreover, a second nebulizer unit is saved.

In a preferred embodiment, at least one device parameter and/or ventilation parameter is registered over time by each of the ventilator and the coughing device. In particular, the registered device parameters and/or ventilation parameters are exchanged between the coughing device and the ventilator in at least one direction. In this case, at least one joint visualization of the device parameters and/or ventilation parameters is preferably displayed before and/or after and/or during a coughing maneuver, so that the effect of the coughing maneuver can be monitored. Additionally or alternatively to the joint visualization, another suitable analysis of the registered data can also be provided.

In a preferred refinement, at least one notification of the coupling is displayed in each of the respiratory therapy devices operationally connected and/or coupled to one another. In particular, the respective display unit is used for this purpose. A menu for adapting the coupling is preferably provided on at least one of the at least two respiratory therapy devices. For example, an input is required as a confirmation to maintain the coupling and/or to deactivate the coupling. The notification is preferably blanked out again upon decoupling. Deactivated device components are preferably also reactivated in particular upon decoupling. In particular, the display unit and/or the operating unit become active again upon decoupling, if they were previously deactivated.

At least one coupling mode from a group of coupling modes is preferably selected in the menu. The coupling modes describe in particular spatial and/or functional arrangements of the coupled respiratory therapy devices. The group preferably comprises at least one arrangement of the coupled respiratory therapy devices one over another and adjacent to one another and back-to-back. The group can also comprise an arrangement in succession and other arrangements.

It is possible that at least one receptacle apparatus is provided for the respiratory therapy devices to be coupled. The receptacle apparatus can comprise an indirect and/or also a direct connection of the two respiratory therapy devices. In this case, a coupling can take place automatically if the respiratory therapy devices are inserted into the receptacle apparatus.

The coupling unit is suitable and designed in particular for the purpose of controlling at least the control units of the at least two respiratory therapy devices in such a way that the device component of the one respiratory therapy device is at least partially functionally expandable and/or replaceable by the device component of the other respiratory therapy device. In particular, the coupling unit is suitable and designed for the purpose of at least partially providing at least one device function of the one respiratory therapy device by means of at least one device component of the other respiratory therapy device.

In particular, the respiratory therapy devices are operationally connectable to one another by means of the coupling unit. The coupling unit comprises in particular at least one interface for the operational connection of the respiratory therapy devices. For example, an electronic data transmission interface is provided. The data transmission can be carried out in a wireless and/or wired manner. The coupling unit is operationally connected in particular to the device components. In particular, the coupling unit can control the control units in such a way that the corresponding device functions can be provided by means of the device components.

The respiratory therapy devices are in particular each equipped with a housing unit. Separate respiratory therapy devices are understood in particular as respiratory therapy devices each having a housing unit. In particular, the two respiratory therapy devices can each be used separately and independently of one another on a patient. In particular, the respiratory therapy devices are transportable independently and separately of one another.

The device component comprises in particular at least one display unit and/or operating unit and/or therapy unit and preferably at least one ventilating unit and/or coughing unit or is designed as such a unit.

In the scope of the present invention, a ventilation parameter is preferably also understood as a coughing parameter and/or a parameter of a coughing therapy. The ventilation parameter is, for example, a pressure or a flow or a volume or the like. The ventilation parameter can also describe those variables as a function of time or as a function of another reference parameter. The ventilation parameter can also be descriptive of the respiratory activity of the patient, for example, the respiration volume or the like. The ventilation parameter can also be registered by sensors directly or indirectly on the patient.

In the scope of the present invention, a device parameter is understood in particular as a variable which is settable or is set on the respiratory therapy device. For example, the device parameter describes a speed of a blower of the ventilating unit or the coughing unit. The device parameter can also describe another variable settable on the device or a control variable for a device component. The device parameter can also comprise a configuration setting.

The present invention also provides a respiratory therapy device for the above-described respiratory therapy system. The respiratory therapy device is preferably designed as described above. In particular, the respiratory therapy device is designed as a coughing device or a ventilator. The respiratory therapy device can in particular be coupled to a ventilator or a coughing device.

BRIEF DESCRIPTION OF THE DRAWINGS

Further advantages and features of the present invention result from the description of the exemplary embodiments, which are explained hereafter with reference to the appended figures.

In the figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
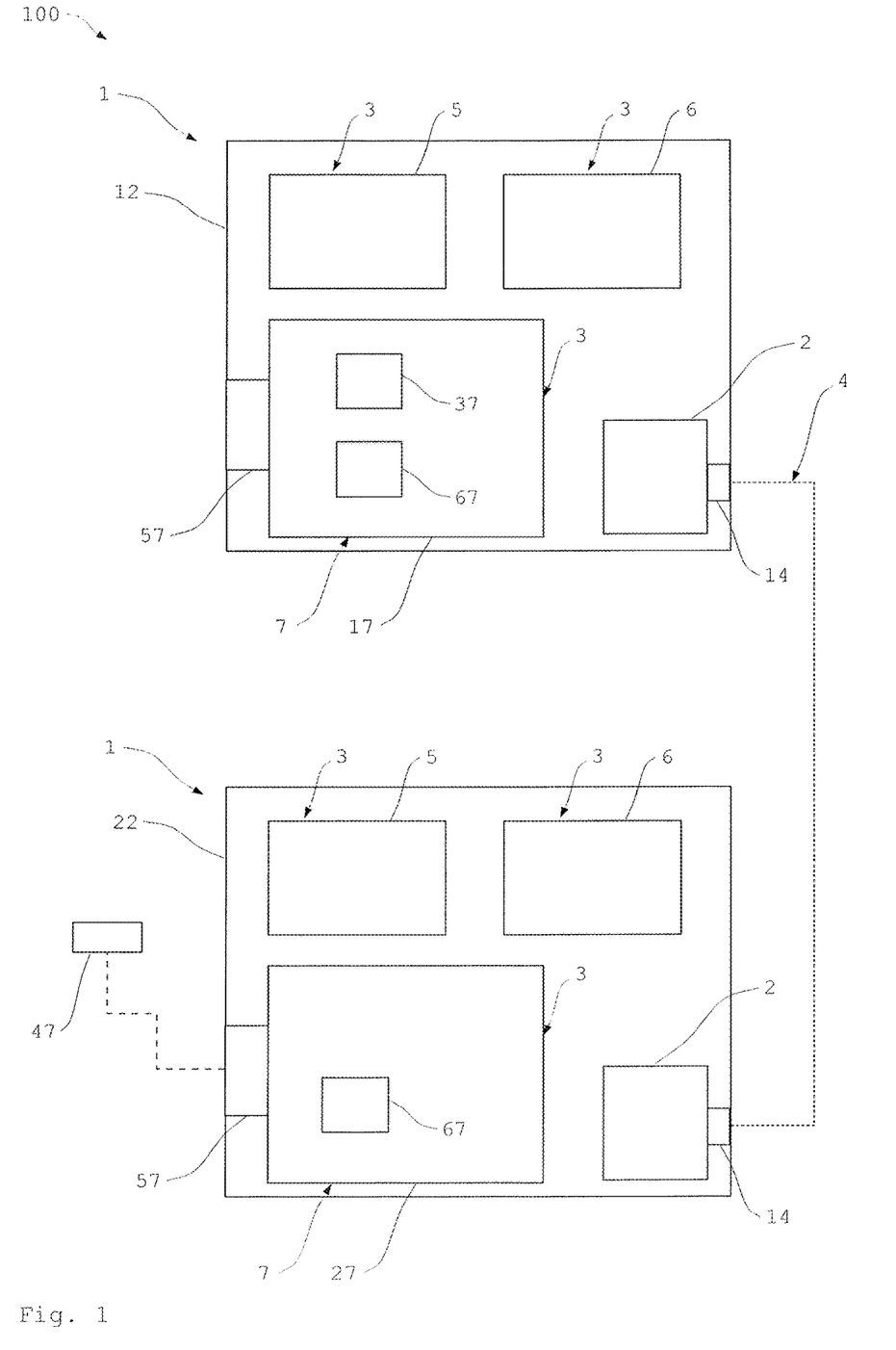
FIG. 1 shows a very schematic illustration of a respiratory therapy system according to the invention.

FIG. 1 shows a respiratory therapy system 100 according to the invention, which comprises two respiratory therapy devices 1 here. The respiratory therapy system 100 is operated as per the method according to the invention. The respiratory therapy devices 1 are provided here by a ventilator 12 and a coughing device 22.

The ventilator 12 comprises a therapy unit 7 here, which is designed as a ventilating unit 17. The ventilating unit 17 is equipped with a blower unit 67 or a fan to generate a respiratory airflow to ventilate the patient. The ventilating unit 17 can additionally comprise at least one valve. The ventilating unit 17 comprises, for example, at least one blower unit 67 and optionally or additionally at least one valve, using which a respiratory airflow for an insufflation and a respiratory airflow for an exsufflation are generated.

The ventilating unit 17 alternatively comprises, for example, two blower units 67 and at least one valve using which a respiratory airflow for an insufflation and a respiratory airflow for an exsufflation are generated. The blower unit and/or the valve are optionally additionally designed and configured to superimpose a respiratory airflow for an insufflation and/or a respiratory airflow for an exsufflation with a defined pulsation. The blower unit and/or the valve are optionally additionally designed and configured to generate the respiratory airflow for an exsufflation in the form of a partial vacuum.

A breathing tube system (not shown in greater detail here) can be connected via a fitting unit 57. Moreover, the ventilating unit 17 comprises here, for example, a nebulizer unit 37, in order to nebulize medications in the respiration air, for example.

The coughing device 22 is used for the targeted assistance of a secretion removal from the airways of a patient and comprises a therapy unit 7 designed as a coughing unit 27 here. The coughing unit 27 comprises, for example, at least one blower unit 67 and optionally additionally at least one valve, using which a respiratory airflow for an insufflation and a respiratory airflow for an exsufflation are generated. The coughing unit 27 alternatively comprises, for example, two blower units 67 and at least one valve, using which a respiratory airflow for an insufflation and a respiratory airflow for an exsufflation are generated. The blower unit and/or the valve are optionally additionally designed and configured to superimpose a respiratory airflow for an insufflation and/or a respiratory airflow for an exsufflation with a defined pulsation, in order to loosen secretions. The blower unit and/or the valve are optionally additionally designed and configured to generate the respiratory airflow for an exsufflation in the form of a partial vacuum, to thus assist the coughing of a patient effectively.

A tube system (not shown in greater detail here), which is suitable for the coughing maneuver and/or a coughing therapy, can be connected via a fitting unit 57. The tube system comprises, for example, an exhalation system 47.

Exhalation air can be continuously discharged via this, for example. The discharge of exhalation air can also be selectively adapted to respiration phases and/or coughing phases, however. In order to enable further device functions in addition to a therapy function, the respiratory therapy devices 1 are equipped here with further device components 3. Thus, each respiratory therapy device 1 has here a display unit 5 and an operating unit 6 for performing inputs and settings. The display unit 5 comprises, for example, a monitor or display. A touchscreen can also be provided. The respiratory therapy devices 1 can have further device components 3 (not shown in greater detail here). The respiratory therapy devices 1 each comprise one or more control units 2 here for controlling the device components 3.

The device components 3 can also partially have independent or separate control units. Presets for controlling the device components 3 are preferably saved or stored in the control unit 2. These presets can be at least partially adapted in particular by the user or a caregiver. The control unit 2 comprises, for example, at least one controller and/or other control components.

The respiratory therapy system 100 has a coupling unit 4 to be able to establish an operational connection between the respiratory therapy devices 1. An interface 14 or connecting interface can be arranged, for example, in each respiratory therapy device 1 for the coupling unit 4. The respiratory therapy devices 1 can communicate in a wireless and/or wired manner via the interfaces 14. The interfaces 14 are preferably operationally connected to the control units 2. The coupling unit 4 is suitable and designed for the purpose of controlling the control units 2 of the respiratory therapy devices 1 when the operational connection is established. The coupling unit 4 can be designed as wired or wireless, for example, as a USB or Bluetooth connection. The coupling unit 4 can alternatively also be designed as a plug connection between the respiratory therapy devices.

The respiratory therapy system 100 offers the option here of functionally expanding or replacing one or more device components 3 of one respiratory therapy device 1 by way of a corresponding device component 3 of the other respiratory therapy device 1 via the coupling unit 4.

In FIGS. 2A, 2B and 3 to 5, the respiratory therapy system 100 is shown having coupled respiratory therapy devices 1, which are arranged in various coupling modes. The observer position and the viewing angle of a user are indicated by a circle and an arrow, respectively.

Figure 2A:
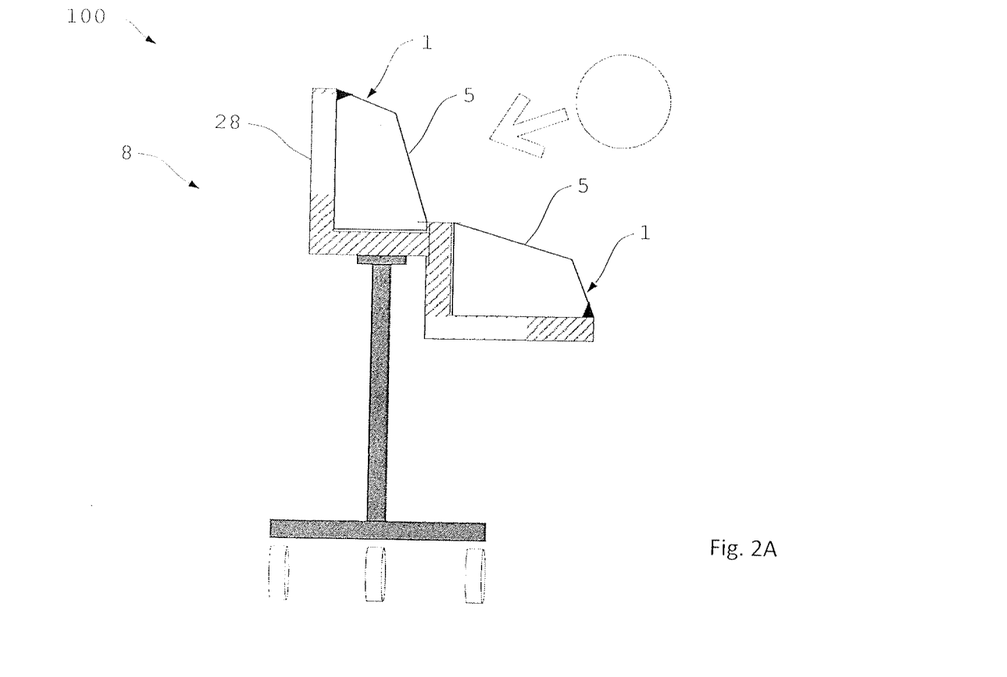
FIGS. 2A and 2B show very schematic illustrations of coupling modes of a respiratory therapy system.

A receptacle apparatus 8 for physically receiving the respiratory therapy devices 1 in a common receptacle unit 28 is shown in FIG. 2A. The receptacle apparatus 8 can also be designed for indirect physical connection of the respiratory therapy devices 1 to the receptacle unit 28. The respiratory therapy devices 1 then have identical, mechanical connecting elements which enable a mechanical coupling to coupling means of the receptacle unit 28. The mechanical connecting elements are embodied as female, for example, and the coupling means are embodied as male. In addition, the mechanical connecting elements and the coupling means can have mechanical catch means.

The receptacle unit 28 is equipped here with a chassis. One respiratory therapy device 1 is positioned upright here, while the other respiratory therapy device 1 is arranged recumbent. The receptacle apparatus 8 can also be designed for the direct physical connection of the respiratory therapy devices 1. The respiratory therapy devices 1 then have mechanical connecting elements complementary to one another, which enable a mechanical coupling of both respiratory therapy devices 1.

The display units are equipped, for example, with position sensors, so that the display units adapt the mode of display to the positioning of the respiratory therapy device.

Figure 2B:
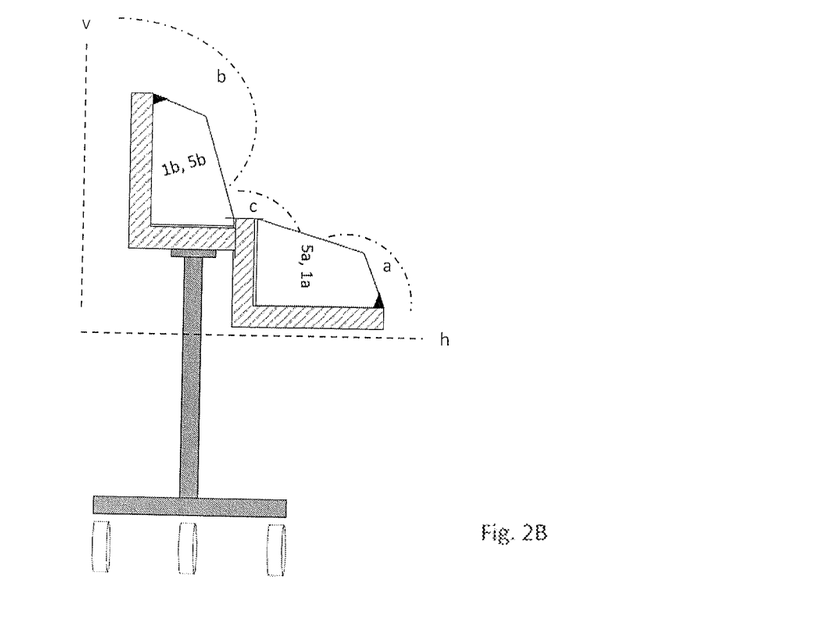

One particular advantage becomes clear in this arrangement. FIG. 2B shows: The display unit 5a of the one respiratory therapy device 1a is arranged inclined at an angle (a) to a horizontal (h). This angle is in the range of 4° to 25°, preferably 6° to 18°, particularly preferably 9° to 15° in relation to the horizontal.

The display unit 5b of the other respiratory therapy device 1b is arranged inclined at an angle (b) in relation to a vertical (v). This angle is in the range of 4° to 25°, preferably 6° to 18°, particularly preferably 9° to 15° in relation to the vertical. Therefore, both display units can be read well by an observer (B).

The display units 5a and 5b have an angle (c) in relation to one another which is greater than 90°, preferably 92° to 102°, particularly preferably 92° to 132°, very particularly preferably 92° to 162°. Therefore, both display units can be read well jointly by an observer (B). The respiratory therapy devices are preferably oriented in such a way that the lower edge of one display unit is essentially at the same height as the upper edge of the other display unit.

The display units 5 can be oriented in this case to the respective position. In this coupling mode, for example, both display units 5 are active, so that an expanded display can be performed.

Figure 3:
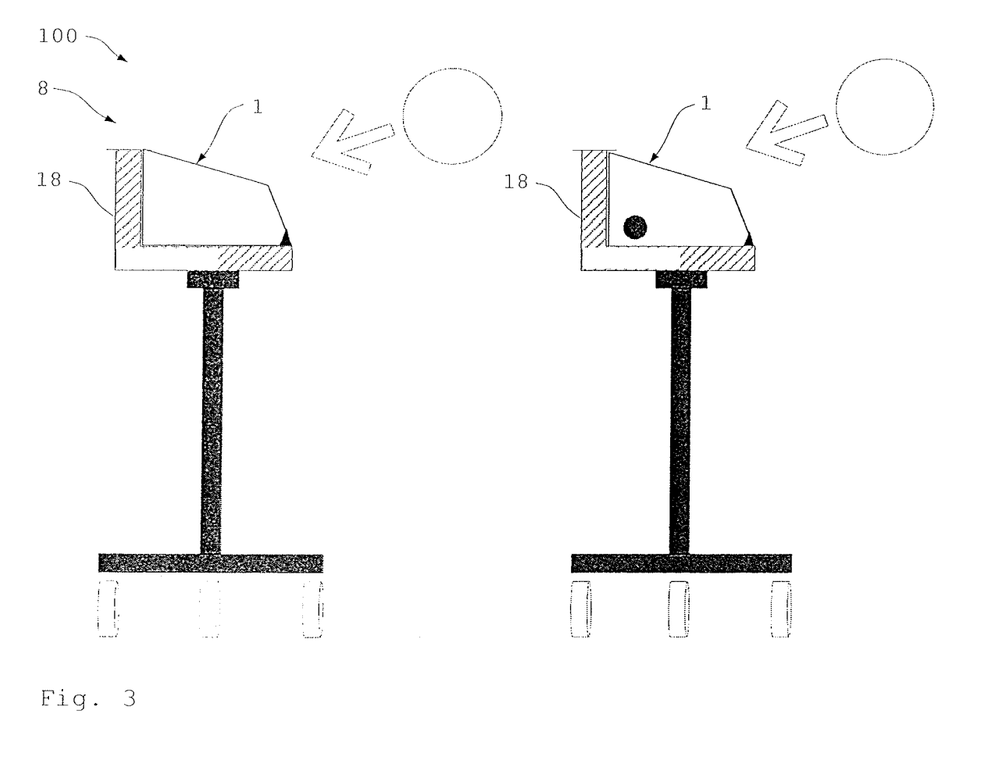
FIG. 3-5 show very schematic illustrations of further coupling modes.

A receptacle apparatus 8 is shown in FIG. 3, which comprises one receptacle unit 18 having a chassis for each respiratory therapy device 1.

Figure 4:
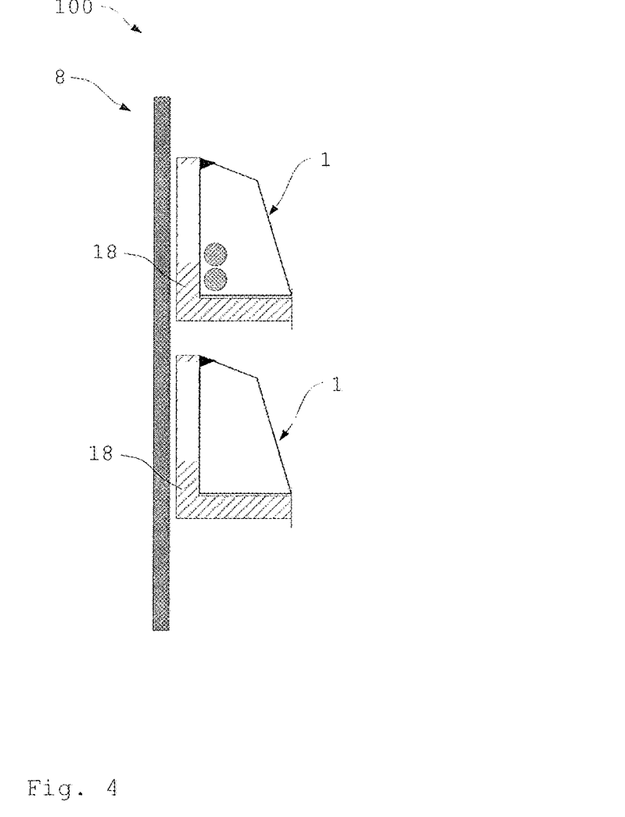

FIG. 4 shows the receptacle units 18 in a wall mounting. In this case, the respiratory therapy devices 1 can be arranged, for example, one over the other or adjacent to one another.

Figure 5:
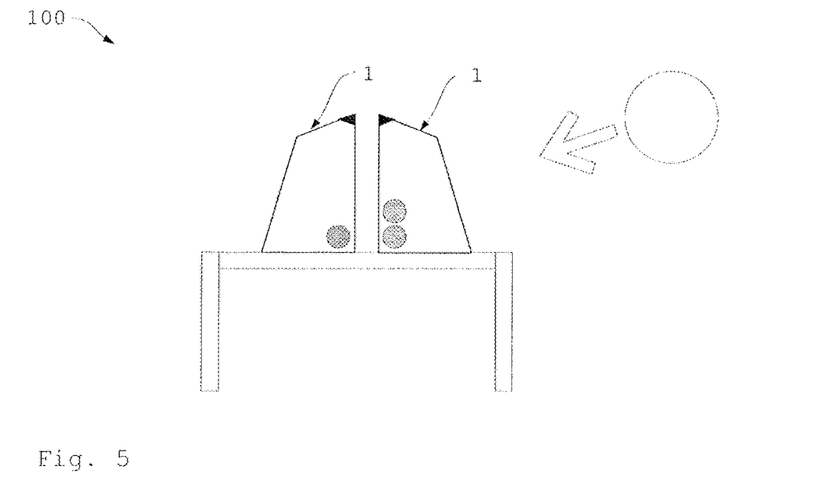

A coupling mode without a physical coupling of the respiratory therapy devices 1 is shown in FIG. 5. For example, the respiratory therapy devices 1 stand on a table or the like in this case. The respiratory therapy devices 1 are arranged back-to-back here. One of the display units 5 is preferably deactivated in this case.

In one example, the ventilator 12 is coupled to the coughing device 22 for control, data visualization, and data analysis.

In one example, it is coupled to the coughing device 22 for control, data visualization, and data analysis.

Data from the coughing device 22 can thus be transmitted to the ventilator 12, wherein the data memory of the ventilator 12 is used for data from the ventilator 12 and for data from the coughing device 22. The ventilator supplies an item of time information in this case, which is stored with the data. If the coughing device also supplies data with an item of time information, this time information of the coughing device is scaled to the time information of the ventilator. The data of ventilator and coughing device thus chronologically stored can be read out and visualized by software or transferred via remote data transfer or read out and processed by a user. Due to the joint analysis of ventilation and coughing data in one piece of software, it is possible to better judge the effects of the therapy. For example, a patient is ventilated and the physiological values worsen (noticeable from lower inspiration volume and low oxygen saturation (SpO2)). A coughing maneuver is then carried out and possibly fixed secretion is loosened. The fact that the coughing therapy was successful can be established, for example, from the measured peak flow in the exhalation (PCF—peak cough flow). Ventilation is then performed again and the physiological values are measured again. It can thus be observed what type of influence a coughing maneuver had.

The coughing device 22 can thus be used as an additional monitor for the ventilator 12. The coughing device 22 can be connected to the ventilator 12 and is used as an additional monitor, in which various ventilation parameters can be displayed. In this case, for example, both devices are fixedly and in particular detachably installed on a chassis or a wall mount.

Different data can be displayed on different display units to display more data overall.

For example, data from the ventilator 12 such as pressures, flow, volume, oxygen content in the blood, each over time, but also pressure over flow or pressure over volume can be recorded by the ventilator and displayed on the display unit 5 of both the ventilator 12 and the coughing device. It is preferably provided in this case that specific data and measured values from the ventilator are displayed on the display unit 5 of the ventilator and other data and measured values of the ventilator are displayed on the display of the coughing device.

Specific data relevant to the observer can be displayed on each of the two display units. For the medical professional, for example, pressure and flow curves can be displayed on the display unit 5 of the ventilator 12 and simplified signals or symbols (for example, arrows) for the inspiration and expiration of the patient can be displayed on the display unit 5 of the coughing device.

The invention offers the advantage that the items of information can be prepared spatially isolated and separately depending on the observer. In contrast to the case of only one monitor (which only reproduces the values), they can also be processed accordingly here.

In particular, different levels are possible, which supplement the operation. Both display units can be operated to interact with the data, for example, by typing and stopping or zooming in the respective region.

Thus, for example, a curve view of the ventilation without superposition of the ventilator monitor can be performed. For example, starting and stopping of an automatic mode can be performed from the ventilator 12, so that the coughing device 22 does not have to be operated. Moreover, the manual mode can also be started from the ventilator 12, so that the coughing maneuver can then be triggered with the aid of a remote control. The signal profile of pressure and flow is shown during this on the ventilator 12.

The coughing maneuver itself can also be operated from the ventilator 12. This means the determination of the points in time of the insufflation, exsufflation, and pause by an operation directly on the ventilator 12.

For example, a parameter setting for the coughing device 22 can be performed in the ventilator 12. The setting/control of various parameters of the coughing device 22 is performed by means of the ventilator 12. The transfer of the set ventilation parameters for the respiratory assistance can be performed, for example, in the coughing device 22.

Furthermore, a time-based or individual notification/reminder adapted to the user can be performed via the ventilator 12, which notifies of an imminent/further performance of the therapeutic respiratory assistance by means of coughing device 22. Thus, for example, a registration by sensors of parameters—such as flow, pressure, oxygen saturation, frequency, and volume—during the ventilation and analysis of these parameters individually for the patient can be performed. From a comparison of these parameter values over a specific period of time, of hours or days or weeks, the ventilator 12 can identify a possible worsening of the patient respiration and thereupon generate a warning notification or a recommendation to use the coughing device 22.

An integrated nebulizer 37 can potentially also be activated to prepare for the coughing up by medication nebulizing.

The shutdown of the coughing device 22 can also be performed via the ventilator 12 (energy saving mode).

One particular advantage is that only one device is used and/or operated. This offers a space-saving setup and simplifies the coughing application.

A joint data visualization with a data transfer from the coughing device 22 to the ventilator 12 and thus a better analysis of the signal profiles of a patient can also occur in the context of both therapies. For example, a potential positive effect of the coughing up of secretion on the following ventilation values (above all volume) can be observed better in context (before/after visualization).

Upon the coupling and/or when the devices 1 are connected, for example, a coupling symbol appears in both devices 1. A message appears in both devices 1, for example, that the coupling was established. In one of the devices 1 and, for example, in the ventilator 12, a message or user input offers the option of changing the coupling mode. The coupling mode is thus settable, for example, in a system menu.

The connection can be implemented in multiple coupling modes.

The last-used coupling mode is preferably always active upon coupling.

For example, in the case of a back-to-back arrangement, the monitor or display screen of one device 1 and in particular of the coughing device 22 is switched off. The therapy of the coughing device 22 may then be started and ended via the ventilator 12 or the remote control and, for example, a housing switch. The function of remotely controlling the coughing device 22 is available in the display of the ventilator 12. The function simulates the home display screen of the coughing device 22, for example. The coughing therapy can now be started and stopped. For example, the therapy program of the coughing device 22 can be selected or set. Therapy measured values of the coughing device are displayed. The start and the stop of the coughing therapy are noted in the event list of the ventilator 12. In this case, the ventilation or ventilating of the ventilator 12 can be active simultaneously.

For example, with an arrangement of the devices 1 one over another or adjacent to one another, both display screens are active. Both devices 1 are usable in the familiar manner thereof. The function of expanding the display screen is available on the display screen of the ventilator 12. If the function is deactivated, the user interface thereof is usable in the display of the coughing device 22. If the function is activated, a curve view of the ventilator 12 is visible in the display of the coughing device 22. The curve view on the ventilator 12 in particular does not display any curves, but rather indicates the active function, and that the contents are displayed on the coughing device 22.

If the devices 1 are decoupled, for example, the display units 5 of both devices 1 are active. The coupling symbol disappears in both devices 1. A message that the connection was decoupled appears in both devices 1.

The present invention offers a coupling/interaction of ventilator and coughing device, which were heretofore used independently of one another. To improve the usage, one device 1 can be switched into the standby mode as soon as the use of the respective other device 1 is recognized. Moreover, a synchronization of data in the case of mobile use of the devices, for example, is enabled. Better handling and an expanded functionality of both devices 1 are achieved when they are coupled.

What is claimed is:

1. A respiratory therapy system, wherein the respiratory therapy system comprises at least two respiratory therapy devices which are operable separately and independently of one another, the at least two respiratory therapy devices each comprising at least one control unit and at least one device component which is controllable by the at least one control unit to provide at least one device function, wherein at least one coupling unit is provided for establishing an operational connection between the at least two respiratory therapy devices, the at least one coupling unit being configured for controlling the control units of the at least two respiratory therapy devices when the operational connection is established, and wherein at least one device component of a first respiratory therapy device is at least partially functionally expandable and/or at least partially functionally replaceable by at least one device component of a second respiratory therapy device by the coupling unit.

2. The system of claim 1, wherein at least one respiratory therapy device is a ventilator and at least one other respiratory therapy device is a coughing device, the ventilator comprising a therapy unit which is a ventilating unit equipped with a blower unit and/or a valve, and the coughing device being configured for targeted assistance of secretion removal from airways of a patient and comprising a therapy unit which is a coughing unit which comprises at least one blower unit and at least one valve.

3. The system of claim 1, wherein at least one display unit of the first respiratory therapy device is at least partially functionally expandable and/or replaceable by at least one display unit of the second respiratory therapy device.

4. The system of claim 3, wherein the display units of the operationally-connected respiratory therapy devices are each capable of being oriented in consideration of a spatial location of the respiratory therapy devices.

5. The system of claim 1, wherein at least one operating unit of at the first respiratory therapy device is at least partially functionally expandable and/or replaceable by at least one operating unit of the second respiratory therapy device and wherein a therapy unit of the second respiratory therapy device is controllable from the operating unit of the first respiratory therapy device.

6. The system of claim 1, wherein at least one therapy unit of the first therapy device is at least partially functionally expandable and/or replaceable by at least one therapy unit of the second respiratory therapy device.

7. The system of claim 6, wherein, by means of the coupling unit, a therapy unit of the first respiratory therapy device can be synchronized with a therapy unit of the second respiratory therapy device at least in consideration of at least one device parameter and/or ventilation parameter.

8. The system of claim 6, wherein a therapy unit of the first or second respiratory therapy device is configured to control, by means of the coupling unit, at least one nebulizer unit arranged in the second or first respiratory therapy device.

9. The system of claim 6, wherein a therapy unit of the first or second respiratory therapy device is configured to control, by means of the coupling unit, an exhalation system of the second or first respiratory therapy device.

10. The system of claim 6, wherein a therapy unit of the first or second respiratory therapy device is connectable to at least one expiration part of the second or first respiratory therapy device to establish a flow connection, in order to be used as a partial vacuum unit for exhalation in an expiration when an operational connection is established.

11. The system of claim 1, wherein the coupling unit is configured for at least partially deactivating and/or activating the device component of the first respiratory therapy device and/or the device component of the second respiratory therapy device when the respiratory therapy devices are operationally connected.

12. The system of claim 1, wherein the system comprises at least one receptacle apparatus for physically receiving the at least two respiratory therapy devices, the at least one receptacle apparatus comprising at least one receptacle unit for each of the respiratory therapy devices and/or comprising at least one joint receptacle unit for the respiratory therapy devices.

13. The system of claim 12, wherein at least two respiratory therapy devices are arranged in the receptacle apparatus in such a way that a display unit of the first respiratory therapy device is arranged inclined at an angle in relation to a horizontal and this angle is in the range of from 4° to 45°, and wherein a display unit of the second respiratory therapy device is arranged inclined at an angle in relation to a vertical and this angle is in the range of from 4° to 45°.

14. The system of claim 13, wherein the respiratory therapy devices are arranged in the receptacle apparatus in such a way that the display units have an angle in relation to one another which is greater than 90°.

15. The system of claim 12, wherein the respiratory therapy devices are arranged in the receptacle apparatus in such a way that a lower edge of one display unit is at about the same height as an upper edge of the other display unit.

* * * * *